(12) United States Patent
Johansen

(10) Patent No.: US 6,251,386 B1
(45) Date of Patent: *Jun. 26, 2001

US006251386B1

(54) ANTIMICROBIAL COMPOSITION CONTAINING A HALOPEROXIDASE, A HYDROGEN PEROXIDE SOURCE, A HALIDE SOURCE AND AN AMMONIUM SOURCE

(75) Inventor: Charlotte Johansen, Holte (DK)

(73) Assignee: Novo Nordisk A/S, Bagsuaerd (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 42 days.

(21) Appl. No.: 09/133,149

(22) Filed: Aug. 12, 1998

Related U.S. Application Data (63) Continuation of application No. 09/133,149, filed on Aug. 12, 1998.
(60) Provisional application No. 60/056,622, filed on Aug. 20, 1998.

(30) Foreign Application Priority Data

Aug. 14, 1997 (DK) .................................................. 0940/97

(51) Int. Cl.⁷ .............................. C12N 9/08; A61K 37/50
(52) U.S. Cl. ..................... 424/94.4; 424/94.1; 424/401; 435/189; 435/190; 435/192; 435/263; 422/28; 8/107

(58) Field of Search ................................. 424/94.1, 94.4, 424/401; 435/189, 263, 190, 192; 422/28; 8/107

(56) References Cited

U.S. PATENT DOCUMENTS

| | | | |
|---|---|---|---|
| 3,539,502 | * 11/1970 | Cantor | 252/106 |
| 5,227,161 | 7/1993 | Kessler. | |
| 5,389,369 | * 2/1995 | Allen | 424/94.4 |
| 5,928,380 | * 7/1999 | Winkler | 8/107 |

FOREIGN PATENT DOCUMENTS

| | | |
|---|---|---|
| 0 500 387 | 8/1992 | (EP). |
| WO 94/04127 | 3/1994 | (WO). |
| WO 94/05252 | 3/1994 | (WO). |
| WO 95/27046 | 10/1995 | (WO). |
| WO 96/38548 | 12/1996 | (WO). |
| WO 97/42825 | 11/1997 | (WO). |

* cited by examiner

*Primary Examiner*—Irene Marx
(74) *Attorney, Agent, or Firm*—Jason I. Garbell, Esq.

(57) ABSTRACT

An enzymatic antimicrobial composition comprising a haloperoxidase, a hydrogen peroxide source, a halide source, and an ammonium source, in particular an ammonium salt or an aminoalcohol, in which there is a hitherto unknown synergistic effect between the halide and the ammonium source.

9 Claims, 5 Drawing Sheets

ANTIMICROBIAL COMPOSITION CONTAINING A HALOPEROXIDASE, A HYDROGEN PEROXIDE SOURCE, A HALIDE SOURCE AND AN AMMONIUM SOURCE

CROSS-REFERENCE TO RELATED APPLICATIONS

This application is a continuation of application Ser. No. 09/133,149 filed Aug. 12, 1998 and claims priority under 35 U.S.C. 119 of U.S. provisional application 60/056,622 filed Aug. 20, 1998 and Danish application 0940/97 filed Aug. 14, 1997, the contents of which are fully incorporated herein by reference.

The present invention relates to a very effective enzymatic composition capable of killing or inhibiting microbial cells or microorganisms, more specifically microbial cells or microorganisms present in laundry, on hard surfaces, in water systems, on skin, teeth or mucous membranes; and for preserving food products, cosmetics, paints, coatings, etc.

BACKGROUND OF THE INVENTION

Various enzymatic antimicrobial compositions are known in the art. For instance, WO 94/04127 discloses stabilized dentifrice compositions which are capable of producing antimicrobially effective concentrations of hypothiocyanite ions. The compositions contain an oxidoreductase capable of producing hydrogen peroxide and a peroxidase enzyme capable of oxidizing thiocyanate ions, which are normally present in saliva, to antimicrobial hypothiocyanite ions. Suitable peroxidases include lactoperoxidase, myeloperoxidase, salivary peroxidase and chloroperoxidase.

In EP-A-0 500 387 enzymatic antimicrobial compositions are disclosed comprising a haloperoxidase, e.g., myeloperoxidase, eosinophil oxidase, lactoperoxidase and chloroperoxidase, which selectively binds to and inhibits the growth of target microorganisms in the presence of peroxide and halide.

WO 95/27046 discloses an antimicrobial composition comprising a Vanadium chloroperoxidase, halide ions, and hydrogen peroxide or a hydrogen peroxide-generating agent.

WO 96/38548 discloses an antimicrobial composition comprising a haloperoxidase, a halide ion, a peroxide generating agent and an amino acid type.

The object of the present invention is to provide a composition for killing or inhibiting microbial cells, i.e., for disinfection or preservation, which is easy to use and an effective alternative to the known disinfecting and preserving compositions and methods.

SUMMARY OF THE INVENTION

Surprisingly, it has been found that the combined action of a haloperoxidase, a hydrogen peroxide source, a halide source and an ammonium source results in a hitherto unknown synergistic antimicrobial effect.

Thus, based on these findings, the present invention provides, in a first aspect, an enzymatic antimicrobial composition comprising a haloperoxidase, a hydrogen peroxide source, a halide source and an ammonium source wherein said composition results in a hitherto unknown synergistic antimicrobial effect.

The composition of the invention is useful as antimicrobial ingredient wherever such an ingredient is needed, for example, for the preservation of food, beverages, cosmetics, deodorants, contact lens products, food ingredients or enzyme compositions; as a disinfectant for use, e.g., on human or animal skin, hair, oral cavity, mucous membranes, wounds, bruises or in the eye; for killing microbial cells in laundry; and for incorporation in cleaning compositions or disinfectants for hard surface cleaning, for water treatment, or for disinfection.

Accordingly, in further aspects, the present invention provides a method of inhibiting microorganisms present in laundry, wherein the laundry is treated with a soaking, washing or rinsing liquor comprising this composition; a method of inhibiting microbial growth on a hard surface, wherein the surface is contacted with this composition; a method of inhibiting microbial cells present in industrial water lines; and a method of killing microbial cells present on human or animal skin, mucous membranes, teeth, wounds, bruises or in the eye or inhibiting the growth thereof, wherein the cells to be killed or inhibited on the skin, mucous membrane, teeth, wound or bruise are/is contacted with this composition.

BRIEF DESCRIPTION OF DRAWINGS

The present invention is further illustrated by reference to the accompanying drawings, in which.

DETAILED DESCRIPTION OF THE INVENTION

In the context of the present invention the term "antimicrobial" is intended to mean that there is a bactericidal and/or a bacteriostatic and/or fungicidal and/or fungistatic effect and/or a virucidal effect, wherein The term "bactericidal" is to be understood as capable of killing bacterial cells.

The term "bacteriostatic" is to be understood as capable of inhibiting bacterial growth, i.e. inhibiting growing bacterial cells.

The term "fungicidal" is to be understood as capable of killing fungal cells.

The term "fungistatic" is to be understood as capable of inhibiting fungal growth, i.e. inhibiting growing fungal cells.

The term "virucidal" is to be understood as capable of inactivating virus.

The term "microbial cells" denotes bacterial or fungal cells, and the term microorganism denotes a fungus (including yeasts) or a bacterium.

In the context of the present invention the term "inhibiting growth of microbial cells" is intended to mean that the cells are in the non-growing state, i.e., that they are not able to progate.

The term "hard surface" as used herein relates to any surface which is essentially non-permeable for microorganisms. Examples of hard surfaces are surfaces made from metal, e.g., stainless steel, plastics, rubber, board, glass, wood, paper, textile, concrete, rock, marble, gypsum and ceramic materials which optionally may be coated, e.g., with paint, enamel and the like. The hard surface can also be a process equipment, e.g., a cooling tower, an osmotic membrane, a water treatment plant, a dairy, a food processing plant, a chemical or pharmaceutical process plant. Accordingly, the composition according to the present invention is useful in a conventional cleaning-in-place (C-I-P) system.

Haloperoxidases

In the context of the present invention the term "haloperoxidase" is intended to mean an enzyme selected from the group consisting of chloride peroxidase (EC 1.11.1.10), bromide peroxidase, and iodide peroxidase (EC 1.11.1.8).

A chloride peroxidase is an enzyme capable of oxidizing chloride, bromide and iodide ions with the consumption of $H_2O_2$.

A bromide peroxidase is an enzyme capable of oxidizing bromide and iodide ions with the consumption of $H_2O_2$.

A iodide peroxidase is an enzyme capable of oxidizing iodide ions with the consumption of $H_2O_2$.

According to the invention Vanadium haloperoxidases are preferred. Vanadium peroxidases are different from other haloperoxidases in that the prosthetic group in theses enzymes have structural features similar to vanadate (vanadium V), whereas the other haloperoxidases are heme-peroxidases. The Vanadium haloperoxidases disclosed in WO 95/27046 are preferred.

Haloperoxidases form a class of enzymes which are able to oxidize halides (X=Cl—, Br—, or I—) in the presence of hydrogen peroxide to the corresponding hypohalous acid (HOX) according to:

If an appropriate nucleophilic compound is present, a reaction will occur with HOX, which has an antimicrobial effect.

Haloperoxidases have been isolated from various organisms: mammals, marine animals, plants, algae, a lichen, fungi and bacteria (for reference see *Biochimica et Biophysica Acta* 1161, 1993, pp. 249–256). It is generally accepted that haloperoxidases are the enzymes responsible for the formation of halogenated compounds in nature, although other enzymes may be involved.

Haloperoxidases have been isolated from many different fungi, in particular from the fungus group dematiaceous hyphomycetes, such as Caldariomyces, e.g., *C. fumago*, Alternaria, Curvularia, e.g., *C. verruculosa* and *C. inaegualis*, Drechslera, Ulocladium and Botrytis (see U.S. Pat. No. 4,937,192).

According to the present invention a haloperoxidase obtainable from Curvularia, in particular *C. verruculosa* is preferred such as *C. verruculosa* CBS 147.63 or *C. verruculosa* CBS 444.70. Curvularia haloperoxidase and recombinant production hereof is described in WO 97/04102.

Haloperoxidase has also been isolated from bacteria such as Pseudomonas, e.g., *P. pyrrocinia* (for reference see *The Journal of Biological Chemistry* 263, 1988, pp. 13725–13732) and Streptomyces, e.g., *S. aureofaciens* (for reference see Structural Biology 1, 1994, pp. 532–537).

Bromide peroxidase has been isolated from algae (see U.S. Pat. No. 4,937,192).

In use, the concentration of the haloperoxidase may be varied in order to achieve the desired antimicrobial effect in the desired time frame. However, according to the invention the haloperoxidase will normally be added in a concentration of 0.01–100 mg enzyme protein per liter, preferably in a concentration of 0.05–50 mg enzyme protein per liter, more preferably in a concentration of 0.5–10 mg enzyme protein per liter.

Hydrogen Peroxide Sources

According to the invention the hydrogen peroxide needed for the reaction with the haloperoxidase may be achieved in many different ways: It may be hydrogen peroxide or a hydrogen peroxide precursor, such as, e.g., percarbonate or perborate, or a peroxycarboxylic acid or a salt thereof, or it may be a hydrogen peroxide generating enzyme system, such as, e.g., an oxidase and its substrate. Useful oxidases may be, e.g., a glucose oxidase, a glycerol oxidase or an amino acid oxidase. An example of an amino acid oxidase is given in WO 94/25574.

It may be advantageous to use enzymatically generated hydrogen peroxide, since this source results in a relatively low concentration of hydrogen peroxide under the biologically relevant conditions. Low concentrations of hydrogen peroxide result in an increase in the rate of haloperoxidase-catalysed reaction.

According to the invention the hydrogen peroxide source needed for the reaction with the haloperoxidase may be added in a concentration corresponding to a hydrogen peroxide concentration in the range of from 0.01–1000 mM, preferably in the range of from 0.1–100 mM.

Halide Sources

According to the invention the halide source needed for the reaction with the haloperoxidase may be achieved in many different ways, e.g., by adding a halide salt: It may be sodium chloride, potassium chloride, sodium bromide, potassium bromide, sodium iodide, or potassium iodide.

The concentration of the halide source will typically correspond to 0.01–1000 mM, preferably in the range of from 0.05–500 mm.

Ammonium Sources

When adding an ammonium source to the antimicrobial composition (haloperoxidase, hydrogen peroxide, halide), halide amines are formed which results in a 100% bactericidal activity of the enzyme system.

We have thus observed that there is a synergistic effect between the halide and the ammonium source present in the composition (see Example 1, 2 and 4).

The used ammonium source may be compounds of the formula:

wherein the substituent groups R1 and R2, which may be identical or different, independently represent any of the following radicals: hydrogen, halide, sulphate, phenyl, a straight or branched chain alkyl having from 1 to 14 carbon atoms, or a substituted straight or branched alkyl group having from 1 to 14 carbon atoms where the substituent group is located at $C_3$–$C_{18}$ and represent any of the following radicals: hydroxy, halogen, formyl, carboxy, and esters and salts hereof, carbamoyl, sulfo, and esters and salts hereof, sulfamoyl, nitro, amino, phenyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group R3; and which phenyl may furthermore be unsubstituted or substituted with one or more substituent groups R3; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups R3;

which substituent group R3 represents any of the following radicals: halogen, hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidin-1-yl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula the substituent groups R1–R2 may together form a group —B—, in which B represents any of the following groups: (—CHR3—N=N—), (—CH=CH—)$_n$ or (—CH=N—)$_n$ in which groups n-represents an integer of from 1 to 3, R3 is a substituent group as defined. (It is to be understood that if the above mentioned formula comprises two or more R3-substituent groups, these R3-substituent groups may be the same or different).

As used herein, the ammonium compounds may be in their cationic form.

In a preferred embodiment R1 is hydrogen.

In another preferred embodiment R1 is hydrogen and R2 is an alkohol (aminoalcohol), e.g., ethanolamine.

In a further preferred embodiment the ammonium source is an ammonium salt, i.e. any ammonium salt known in the art: e.g., diammonium sulphate, ammonium chloride, ammonium bromide, or ammonium iodide.

According to the invention the ammonium source needed for the reaction with the haloperoxidase may be added in a concentration corresponding to an ammonium concentration in the range of from 0.01–1000 mM, preferably in the range of from 0.05–500 mM.

The Composition

The composition comprising the haloperoxidase, the hydrogen peroxide source, the halide source, and the ammonium source may be formulated as a solid or a liquid.

When formulated as a solid all components may be mixed together, e.g., as a powder, a granulate or a gelled product.

When other than dry form compositions are used and even in that case, it is preferred to use a two part formulation system having the hydrogen peroxide separate from the other components.

The composition of the invention may further comprise auxiliary agents such as wetting agents, thickening agents, buffer, stabilisers, perfume, colourants, fillers and the like.

Useful wetting agents are surfactants, i.e., non-ionic, anionic, amphoteric or zwitterionic surfactants.

The composition of the invention may be a concentrated product or a ready-to-use product. In use, the concentrated product is typically diluted with water to provide a medium having an effective antimicrobial activity, applied to the object to be disinfected or preserved, and allowed to react with the micro-organisms present.

The optimum pH is usually a compromise between the optimum stability and optimum activity of the haloperoxidase in question. However the invention may advantageously be carried out at a relatively high pH, since it is contemplated that the bacteriocidal activities are optimal at high pH values.

The composition of the invention may also be formulated as a two part system wherein one part is the haloperoxidase and the ammonium source; the other part is the hydrogen peroxide source; and the halide source may then come from tap water or otherwise be naturally present.

Uses

The composition of the invention may be incorporated into a detergent or cleaning composition comprising more enzyme types useful in detergent or cleaning compositions, preferably at least one further enzyme selected from the group consisting of proteases, carbohydrases, amylases, cutinases, peroxidases, oxidases, laccases, cellulases, xylanases, and lipases.

When used for preservation of food, beverages, cosmetics such as lotions, creams, gels, ointments, soaps, shampoos, conditioners, antiperspirants, deodorants, mouth wash, contact lens products, enzyme formulations, or food ingredients, the composition used in the method of the present invention may be incorporated into the e.g. unpreserved food, beverages, cosmetics, contact lens products, food ingredients or antiinflammatory product in an amount effective for killing or inhibiting growing of microbial cells.

Thus, the composition used in the method of the invention may by useful as a disinfectant, e.g., in the treatment of acne, infections in the eye or the mouth, skin infections; in antiperspirants or deodorants; in foot bath salts; for cleaning and disinfection of contact lenses, hard surfaces, teeth (oral care), wounds, bruises and the like.

In general it is contemplated that the composition of the present invention is useful for cleaning, disinfecting or inhibiting microbial growth on any hard surface. Examples of surfaces, which may advantageously be contacted with the composition of the invention are surfaces of process equipment used e.g. dairies, chemical or pharmaceutical process plants, water sanitation systems, paper pulp processing plants, water treatment plants, and cooling towers.

The composition of the invention should be used in an amount, which is effective for cleaning, disinfecting or inhibiting microbial growth on the surface in question.

Further, it is contemplated that the composition of the invention can advantageously be used in a cleaning-in-place (C.I.P.) system for cleaning of process equipment of any kind.

The method of the invention may additionally be used for cleaning surfaces and cooking utensils in food processing plants and in any area in which food is prepared or served such as hospitals, nursing homes, restaurants, especially fast food restaurants, delicatessens and the like. It may also be used as an antimicrobial in food products and would be especially useful as a surface antimicrobial in cheeses, fruits and vegetables and food on salad bars.

It may also be used as a preservation agent or a disinfection agent in water based paints.

The composition of the present invention is also useful for microbial control of water lines, and for disinfection of water, in particular for disinfection of industrial water.

The present invention is further illustrated in the following examples which are not in any way intended to limit the scope of the invention as claimed.

EXAMPLE 1

Antibacterial activity of haloperoxidase against *P. aeruginosa* and *S. epidermidis*.

The antibacterial activity of *Curvularia verruculosa* recombinant peroxidase (rCvP), produced as described in WO 97/04102, available from Novo Nordisk A/S, DK-2880 Bagsvaerd, Denmark, has been tested with the following enhancing agents: sodium chloride and diammonium sulphate.

The antibacterial activity of a haloperoxidase was tested in MES-buffer (2-[N-morpholino] ethanesulfonic acid) (pH 6.0) against *Pseudomonas aeruginosa* ATCC 10146 and *Staphylococcus epidermidis* DSM 20 042 with sodium chloride as electron donor, and hydrogen peroxide was added as electron acceptor in the presence of $NH_4^+$. The cells (approximately $10^6$ cfu/ml) were incubated with the enzyme for 15 min at 40° C.

The bactericidal activity was determined by incubation in Malthus. The detection times measured by the Malthus instrument were converted to cfu/ml by a calibration curve.

Either direct or indirect Malthus measurements were used when enumerating total survival cells (Malthus Flexi M2060, Malthus Instrument Limited). By the direct measurements, the cell metabolism was determined by conductance measurements in the growth substrate. By the indirect measurements, 3 ml of growth medium was transferred to the outer chamber of the indirect Malthus cells, and 0.5 ml of sterile KOH (0.1 M) was transferred to the inner chamber. The cell suspensions were after enzyme treatment transferred to the outer chamber of the Malthus cell. As cells are growing in the outer chamber they produce $CO_2$ which will dissolve in the KOH in the inner chamber and thereby change the conductance of the KOH. The amount of $CO_2$ formed by the respiring cells surviving the enzyme treatment was used for estimating the number of viable cells.

Figure 1:
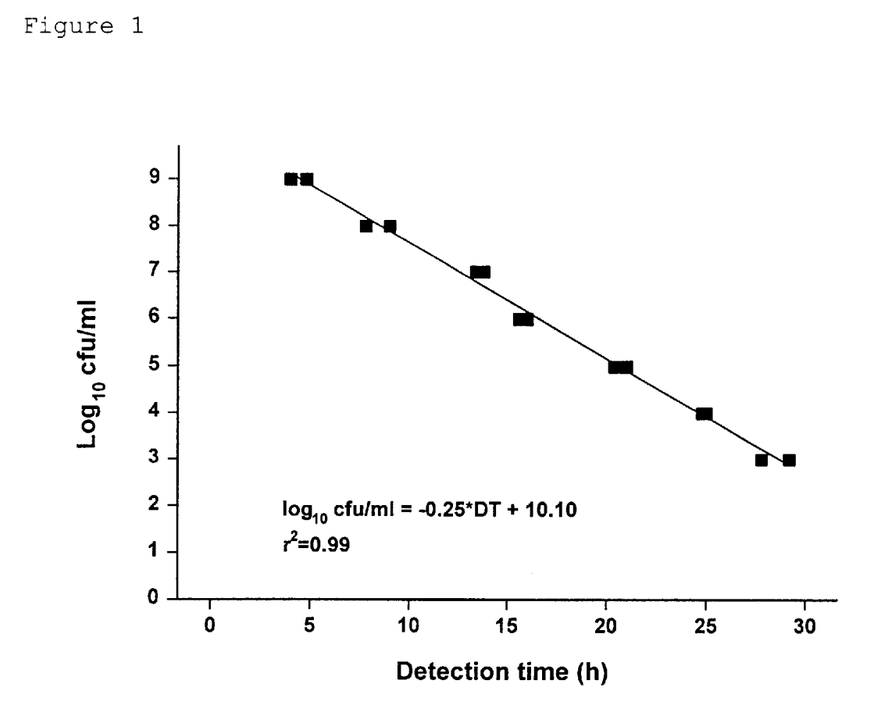
FIG. 1 shows a calibration curve for growth of *Pseudomonas aeruginosa* ATCC 10146 in TSB at 25° C.; see Example 1.

When the conductance change is measurable by the Malthus, a detection time (dt) will be recorded. The dt's were converted to colony counts by use of a calibration curve relating cfu/ml to dt (FIG. 1).

Antibacterial activity of a haloperoxidase (1 mg/l) with NaCl was at pH 6 observed at NaCl concentrations above 20 mM, the antibacterial activity increased with increasing NaCl concentrations but a plateau was reached at approximately 100 mM (depends on pH, temperature, test strains etc.). Hydrogen peroxide was added to a final concentration of 0.5 mM. Using 200 mM NaCl as electron donor resulted in a reduction in living cells (both strains) from $10^6$ cfu/ml to approximately $10^3$ cfu/ml.

Figure 2:
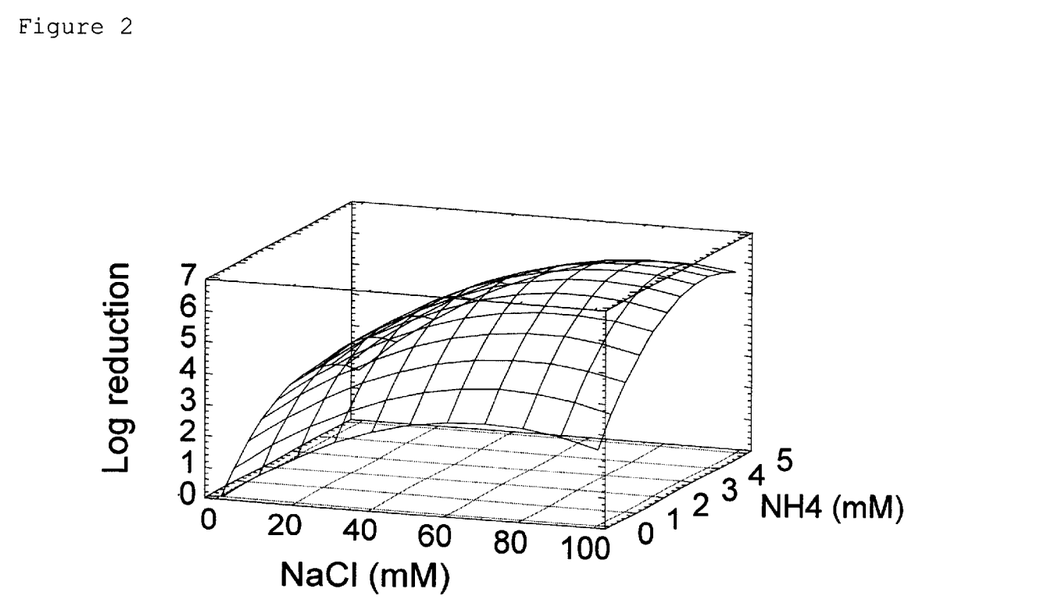
FIG. 2 shows a response surface plot for the antibacterial activity against *Staphylococcus epidermidis*; when sodium chloride and/or ammonium are added to the reaction medium; see Example 1.

A significant synergistic effect was observed between NaCl and $(NH_4)_2SO_4$. The combination of NaCl and $(NH_4)_2SO_4$ resulted in a 100% lethal activity against both strains (FIG. 2) at a concentration of from about 3 mM $NH_4^+$.

EXAMPLE 2

Antibacterial activity of *Curvularia verruculosa* recombinant haloperoxidase using different enhancing agents The antibacterial activity of a haloperoxidase (1 mg/l) was tested in MES-buffer (2-[N-morpholino] ethanesulfonic acid) (pH 6.0) against *Staphylococcus epidermidis* DSM 20 042 with potassium iodide and potassium bromide as electron donor, and hydrogen peroxide (to a final concentration of 0.5 mM) was added as electron acceptor in the presence of $NH_4^+$. The cells (approximately $10^6$ cfu/ml) were incubated with enzyme for 15 min at 40° C. The bactericidal activity was determined by incubation in Malthus (see Example 1).

Figure 3:
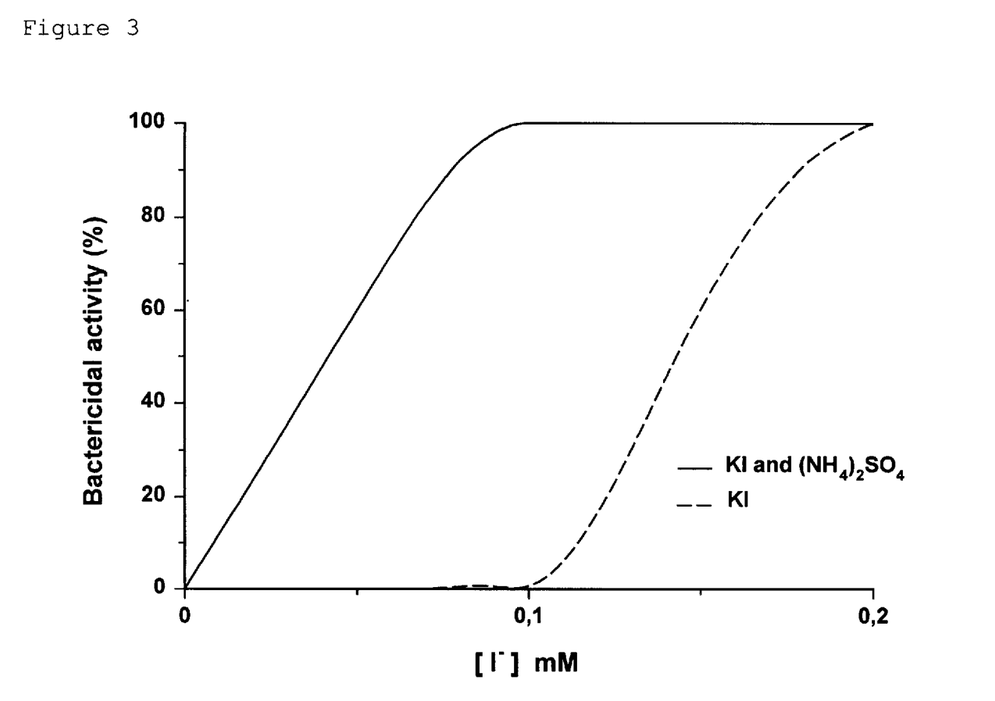
FIG. 3 shows the bactericidal activity of the *Curvularia haloperoxidase* combined with iodide and ammonium sulphate (______: KI and (NH4)2SO4; - - - : KI); see Example 2.

A 100% antibacterial activity of the haloperoxidase combined with iodide was determined at a iodide concentration of about 0.2 mM. If ammonium was added, a 100% bactericidal activity was determined already at a concentration of about 0.05–0.1 mM iodide (FIG. 3).

Figure 4:
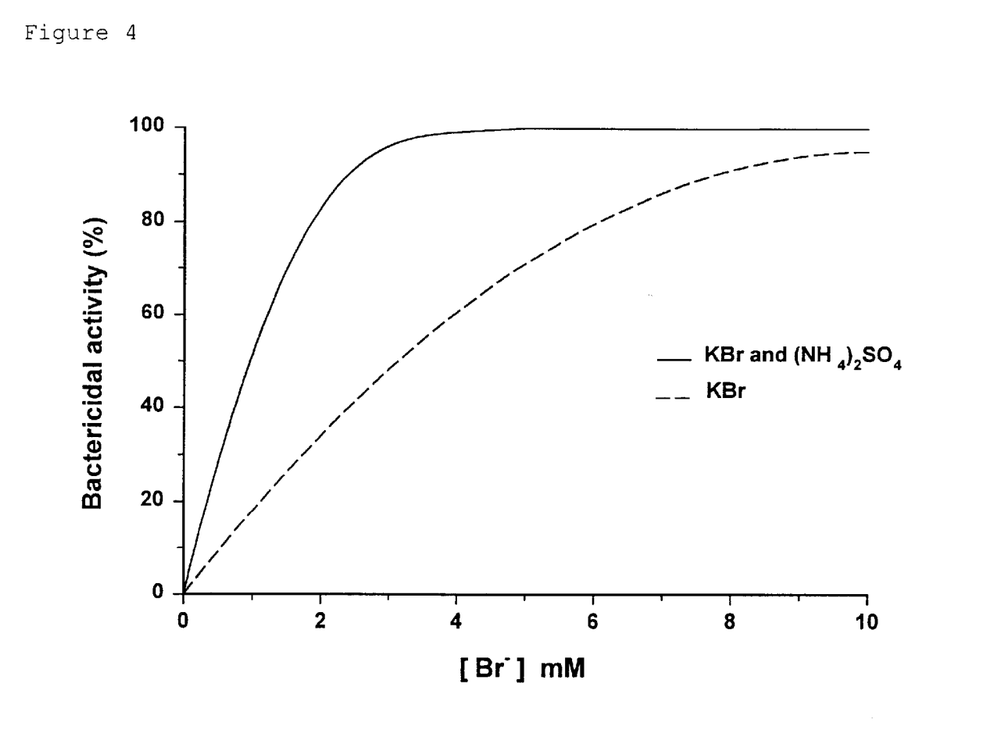
FIG. 4 shows the bactericidal activity of the *Curvularia haloperoxidase* combined with bromide and ammonium sulphate; (______: KBr and (NH4)2SO4; - - - : KBr); see Example 2.

A high concentration of bromide (>10 mM) was needed for 100% bactericidal activity, but the combination of bromide and ammonium ions resulted in a 100% bactericidal activity at a bromide concentration of above 2.5 mM (FIG. 4).

EXAMPLE 3

Antibacterial activity of *Curvularia verruculosa* recombinant haloperoxidase using ammonium halides as electron donors The antibacterial activity of a haloperoxidase (1 mg/l) was tested in MES-buffer (2-[N-morpholino] ethanesulfonic acid) (pH 6.0) against *Staphylococcus epidermidis* DSM 20 042 with ammonium iodide, ammonium chloride or ammonium bromide as electron donors, and hydrogen peroxide was added as electron acceptor giving the final concentration 0.5 mM. The cells (approximately $10^6$ cfu/ml) were incubated with enzyme for 15 min at 40° C. The bactericidal activity was determined by incubation in Malthus (see Example 1).

The concentration of ammonium halides which is needed for antibacterial activity, is below the concentration of potassium or sodium halides needed for the same activity (Table 1).

TABLE 1

Bactericidal activity against *S. epidermidis*. The electron donor is added either as a potassium or sodium salt or an ammonium salt.

| Concentration of halide (mM) | Log reduction in cell number (log cfu/ml) |
|---|---|
| 0 | 0 |
| INH$_4$: | |
| 0.25 | 6.2 |
| 0.5 | 6.2 |

TABLE 1-continued

Bactericidal activity against *S. epidermidis*. The electron donor is added either as a potassium or sodium salt or an ammonium salt.

| Concentration of halide (mM) | Log reduction in cell number (log cfu/ml) |
|---|---|
| KI: | |
| 0.25 | 5.1 |
| 0.5 | 6.1 |
| ClNH$_4$: | |
| 25 | 6.2 |
| 50 | 6.2 |
| NaCl: | |
| 25 | 0.5 |
| 50 | 0.8 |
| BrNH$_4$: | |
| 4 | 3.7 |
| 8 | 6.2 |
| KBr: | |
| 4 | 2.8 |
| 8 | 5.4 |

It can be seen from Table 1 that if the salt is an ammonium halide salt such as ammonium iodide, ammonium chloride, or ammonium bromide a 100% bactericidal activity is possible. So the halide- and the ammonium-source may be one and the same, but normally the optimum concentrations of the halide and the ammonium will be at different levels.

EXAMPLE 4

Synergistic antibacterial activity of *Curvularia verruculosa* recombinant haloperoxidase (rCvP) using ethanolamine in combination with halides The antibacterial activity of *Curvularia verruculosa* (1 mg/L) was tested in HEPES-buffer (Sigma H3375) (pH7.0) against *Staphylococcus epidermidis* DSM 20 042 with chloride (80 mM) as electron donor combined with ethanolamine (2.5 mM), and hydrogen peroxide was added as electron acceptor giving the final concentration 0.5 mM. The synergistic effects were found by using a $2^4$ factorial design. The cells (approximately $10^6$ cfu/ml) were incubated with enzyme for 15 min at 40° C. The bactericidal activity was determined by incubation in Malthus (see Example 1).

Figure 5:
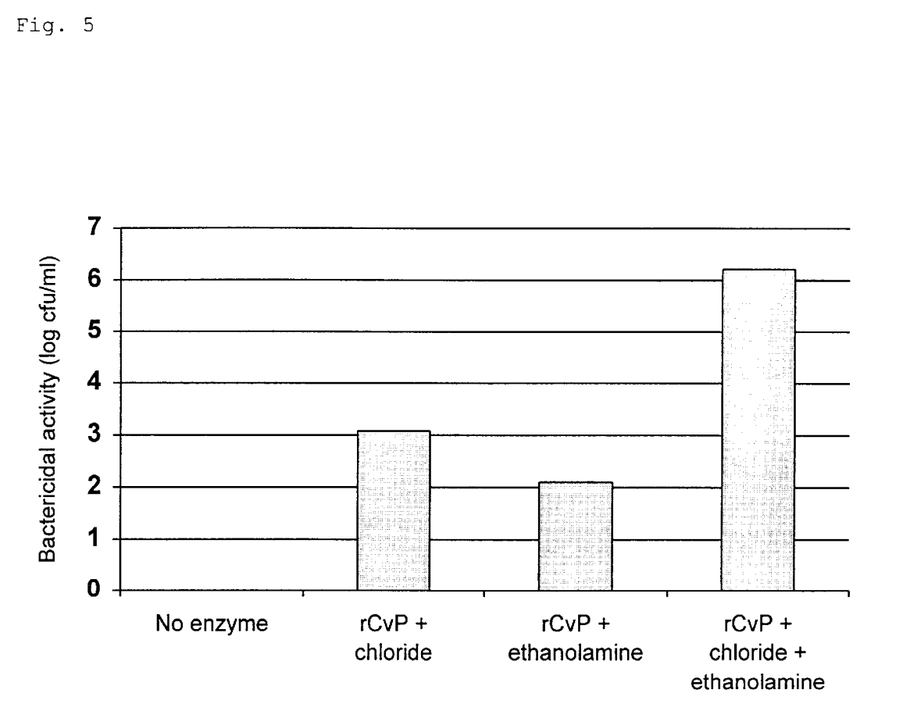
FIG. 5 shows the bactericidal activity of the *Curvularia haloperoxidase* (rCvP) combined with chloride and ethanolamine; see Example 4.

Addition of ethanolamine significantly increased the activity of the enzyme system (see FIG. 5). Thus, a 100% kill was obtained against *Staphylococcus epidermidis* when ethanolamine was added, whereas a cell reduction of approximately 3 log units was observed when no ethanolamine was added.

What is claimed is:

1. An enzymatic antimicrobial composition, comprising:
   (a) a *Curvularia verruculosa* haloperoxidase having a concentration in the range of 0.01–100 mg/L;
   (b) hydrogen peroxide having a concentration in the range of 0.01–1000 mM;
   (c) sodium chloride having a concentration in the range of 0.01–1000 mM; and
   (d) diammonium sulfate having a concentration in the range of 0.01–1000 mM.

2. An enzymatic antimicrobial composition, comprising:
   (a) a *Curvularia verruculosa* haloperoxidase having a concentration in the range of 0.01–100 mg/L;
   (b) hydrogen peroxide having a concentration in the range of 0.01–1000 mM; and
   (c) an ammonium halide selected from the group consisting of ammonium iodide, ammonium chloride and ammonium bromide and having a concentration in the range of 0.01–1000 mM.

3. An enzymatic antimicrobial composition, comprising:
   (a) a *Curvularia verruculosa* haloperoxidase having a concentration in the range of 0.01–100 mg/L;
   (b) hydrogen peroxide having a concentration in the range of 0.01–1000 mM;
   (c) chloride having a concentration of in the range of 0.01–1000 mM; and
   (d) ethanolamine having a concentration in the range of 0.01–1000 mM.

4. The composition of claim 1, wherein the haloperoxidase is obtained from *Curvularia verruculosa* CBS 147.63.

5. The composition of claim 2, wherein the haloperoxidase is obtained from *Curvularia verruculosa* CBS 147.63.

6. The composition of claim 3, wherein the haloperoxidase is obtained from *Curvularia verruculosa* CBS 147.63.

7. The composition of claim 1, which is an aqueous composition or a granulate.

8. The composition of claim 2, which is an aqueous composition or a granulate.

9. The composition of claim 3, which is an aqueous composition or a granulate.

* * * * *